(12) United States Patent
Bonrath et al.

(10) Patent No.: US 11,167,270 B2
(45) Date of Patent: Nov. 9, 2021

(54) METAL POWDERDOUS CATALYST FOR HYDROGENATION PROCESSES

(71) Applicant: DSM IP ASSETS B.V., Heerlen (NL)

(72) Inventors: Werner Bonrath, Kaiseraugst (CH); Roman Goy, Kaiseraugst (CH); Jonathan Alan Medlock, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 64 days.

(21) Appl. No.: 16/609,528

(22) PCT Filed: May 1, 2018

(86) PCT No.: PCT/EP2018/061068
§ 371 (c)(1),
(2) Date: Oct. 30, 2019

(87) PCT Pub. No.: WO2018/202639
PCT Pub. Date: Nov. 8, 2018

(65) Prior Publication Data
US 2020/0061587 A1   Feb. 27, 2020

(30) Foreign Application Priority Data
May 1, 2017 (EP) .................................. 17168887

(51) Int. Cl.
| | | |
|---|---|---|
| *B01J 23/74* | (2006.01) | |
| *B01J 23/745* | (2006.01) | |
| *B01J 23/10* | (2006.01) | |
| *B01J 23/26* | (2006.01) | |
| *B01J 23/28* | (2006.01) | |
| *B01J 23/44* | (2006.01) | |
| *B01J 23/75* | (2006.01) | |
| *B01J 23/755* | (2006.01) | |
| *B01J 37/02* | (2006.01) | |

(52) U.S. Cl.
CPC ............. *B01J 23/745* (2013.01); *B01J 23/10* (2013.01); *B01J 23/26* (2013.01); *B01J 23/28* (2013.01); *B01J 23/44* (2013.01); *B01J 23/75* (2013.01); *B01J 23/755* (2013.01); *B01J 37/0201* (2013.01); *B01J 37/0215* (2013.01)

(58) Field of Classification Search
CPC ... B01J 23/10; B01J 23/26; B01J 23/28; B01J 23/44; B01J 23/63; B01J 23/745; B01J 23/75; B01J 23/755; B01J 23/83; B01J 35/0006; B01J 35/006; B01J 37/009; B01J 37/0215; B01J 37/0225; B01J 37/0228; B01J 37/0244; B01J 37/08; B01J 37/16; B01J 37/18; B01J 37/343; C07C 29/17

See application file for complete search history.

(56) References Cited

U.S. PATENT DOCUMENTS

| | | | | |
|---|---|---|---|---|
| 4,006,012 A | * | 2/1977 | Kindlimann | .......... C22C 19/056 420/451 |
| 2003/0036477 A1 | * | 2/2003 | Nordquist | ................ B01J 35/10 502/20 |
| 2004/0199019 A1 | * | 10/2004 | Schmidt | ............... B01J 37/0225 564/480 |
| 2006/0029535 A1 | * | 2/2006 | Ott | ..................... B01D 53/8625 423/239.2 |
| 2014/0106962 A1 | | 4/2014 | Durante et al. | |

FOREIGN PATENT DOCUMENTS

| | | |
|---|---|---|
| EP | 3 231 511 | 10/2017 |
| WO | 2016/092957 | 6/2016 |

OTHER PUBLICATIONS

McGuire, M.F. (2008) Stainless Steels for Design Engineers, ASM International, 296 pgs [Office action references Table 1 on p. 72].*
International Search Report for PCT/EP2018/061068 dated Jul. 24, 2018, 3 pages.
Written Opinion of the ISA for PCT/EP2018/061068 dated Jul. 24, 2018, 3 pages.

* cited by examiner

*Primary Examiner* — Brian A McCaig
(74) *Attorney, Agent, or Firm* — Nixon & Vanderhye P.C.

(57) ABSTRACT

The present invention is related to a new metal powder catalytic system (catalyst), its production and its use in hydrogenation processes.

16 Claims, No Drawings

METAL POWDERDOUS CATALYST FOR HYDROGENATION PROCESSES

This application is the U.S. national phase of International Application No. PCT/EP2018/061068 filed May 1, 2018 which designated the U.S. and claims priority to EP Patent Application No. 17168887.2 filed May 1, 2017, the entire contents of each of which are hereby incorporated by reference.

The present invention is related to a new metal powder catalytic system (catalyst), its production and its use in hydrogenation processes.

Powderous catalysts are well known and used in chemical reactions. Important types of such catalysts are i.e. the Lindlar catalysts.

The Lindlar catalyst is a heterogeneous catalyst which consists of palladium deposited on a calcium carbonate carrier which is also treated with various forms of lead.

Such catalysts are of such an importance that there is always a need for their improvement.

The goal of the present invention was to find a powderous catalyst with improved properties.

The powderous catalysts according to the present invention have a metal (or metal alloy) as carrier material, instead of a calcium carbonate carrier.

This metal alloy is coated by a metal oxide layer on which palladium (Pd) is deposited.

Furthermore the new catalyst according to the present invention is free from lead (Pb). This applies to all powderous catalytic systems, which are part of this patent application.

Therefore, the present invention relates to a powderous catalytic system (I) comprising
a metal alloy carrier comprising
  (i) 45 weight-% (wt-%)-80 wt-%, based on the total weight of the metal alloy, of Fe, and
  (ii) 0.5 wt-%-30 wt-%, based on the total weight of the metal alloy, of Ni, and
  (iii) 0 wt-%-20 wt-%, based on the total weight of the metal alloy, of Co, and
  (iv) 0 wt-%-8 wt-%, based on the total weight of the metal alloy, of Mo, and
  (v) 0 wt-%-30 wt-%, based on the total weight of the metal alloy, of Cr, and
wherein the said metal alloy is coated by a metal oxide layer and impregnated with Pd-nanoparticles,
characterized in that the metal oxide layer comprises $CeO_2$.

It is obvious that all percentages always add up to 100.

Therefore, the present invention relates to a powderous catalytic system (I') consisting of
a metal alloy carrier consisting of
  (i) 45 wt-%-80 wt-%, based on the total weight of the metal alloy, of Fe, and
  (ii) 0.5 wt-%-30 wt-%, based on the total weight of the metal alloy, of Ni, and
  (iii) 0 wt-%-20 wt-%, based on the total weight of the metal alloy, of Co, and
  (iv) 0 wt-%-8 wt-%, based on the total weight of the metal alloy, of Mo, and
  (v) 0 wt-%-30 wt-%, based on the total weight of the metal alloy, of Cr, and
wherein the said metal alloy is coated by a metal oxide layer and impregnated with Pd-nanoparticles,
characterized in that the metal oxide layer comprises $CeO_2$.

The catalytic system is in the form of a powder.

This new catalyst has numerous advantages:

The catalyst is easy to recycle (and to remove) after the reaction. This can be done i.e. by filtration, magnetisation.

The catalyst can be used more than once (re-usable).

The catalyst is easy to produce.

The catalyst is easy to handle.

The hydrogenation can be carried out with or without any solvents.

The catalyst is free from lead.

The catalyst shows high selectivity in hydrogenation reactions.

The metal alloys used are steel types.

The catalytic system is in the form of a powder.

Suitable metal alloys used in the present invention are iron/nickel/cobalt/molybendum alloys. Such alloys are known as maraging steels and can be bought commercially from companies such as Matthey SA (Switzerland) and EOS GmbH (Germany). Such steels are available under the tradenames of Durnco or EOS Maraging Steel MS1.

Suitable iron/nickel/cobalt/molybendum alloys comprise
  (i) 45 wt-%-75 wt-%, based on the total weight of the metal alloy, of Fe, and
  (ii) 15 wt-%-30 wt-%, based on the total weight of the metal alloy, of Ni, and
  (iii) 5 wt-%-20 wt-%, based on the total weight of the metal alloy, of Co, and
  (iv) 3 wt-%-8 wt-%, based on the total weight of the metal alloy, of Mo.

Furthermore, suitable iron/nickel/cobalt/molybendum alloys consist of
  (i) 45 wt-%-75 wt-%, based on the total weight of the metal alloy, of Fe, and
  (ii) 15 wt-%-30 wt-%, based on the total weight of the metal alloy, of Ni, and
  (iii) 5 wt-%-20 wt-%, based on the total weight of the metal alloy, of Co, and
  (iv) 3 wt-%-8 wt-%, based on the total weight of the metal alloy, of Mo.

Therefore, the present invention relates to a powderous catalytic system (II) which is the powderous catalytic system (I), wherein the metal alloy carrier comprises
  (i) 45 wt-%-75 wt-%, based on the total weight of the metal alloy, of Fe, and
  (ii) 15 wt-%-30 wt-%, based on the total weight of the metal alloy, of Ni, and
  (iii) 5 wt-%-20 wt-%, based on the total weight of the metal alloy, of Co, and
  (iv) 3 wt-%-8 wt-%, based on the total weight of the metal alloy, of Mo.

Therefore, the present invention relates to a powderous catalytic system (II') which is the powderous catalytic system (I), wherein the metal alloy carrier consists of
  (i) 45 weight-% (wt-%)-75 wt-%, based on the total weight of the metal alloy, of Fe, and
  (ii) 15 wt-%-30 wt-%, based on the total weight of the metal alloy, of Ni, and
  (iii) 5 wt-%-20 wt-%, based on the total weight of the metal alloy, of Co, and
  (iv) 3 wt-%-8 wt-%, based on the total weight of the metal alloy, of Mo.

Preferred iron/nickel/cobalt/molybendum alloys comprise
  (i) 60 wt-%-70 wt-%, based on the total weight of the metal alloy, of Fe, and
  (ii) 15 wt-%-25 wt-%, based on the total weight of the metal alloy, of Ni, and (iii) 5 wt-%-15 wt-%, based on the total weight of the metal alloy, of Co, and
(iv) 3.5 wt-%-7 wt-%, based on the total weight of the metal alloy, of Mo.

Furthermore, preferred iron/nickel/cobalt/molybendum alloys consist of
(i) 60 wt-%-70 wt-%, based on the total weight of the metal alloy, of Fe, and
(ii) 15 wt-%-25 wt-%, based on the total weight of the metal alloy, of Ni, and
(iii) 5 wt-%-15 wt-%, based on the total weight of the metal alloy, of Co, and
(iv) 3.5 wt-%-7 wt-%, based on the total weight of the metal alloy, of Mo.

Therefore, the present invention relates to a powderous catalytic system (III) which is the powderous catalytic system (I) or (II), wherein the metal alloy carrier comprises
(i) 60 wt-%-70 wt-%, based on the total weight of the metal alloy, of Fe, and
(ii) 15 wt-%-25 wt-%, based on the total weight of the metal alloy, of Ni, and
(iii) 5 wt-%-15 wt-%, based on the total weight of the metal alloy, of Co, and
(iv) 3.5 wt-%-7 wt-%, based on the total weight of the metal alloy, of Mo.

Therefore, the present invention relates to a powderous catalytic system (III') which is the powderous catalytic system (I), wherein the metal alloy carrier consists of
(i) 60 wt-%-70 wt-%, based on the total weight of the metal alloy, of Fe, and
(ii) 15 wt-%-25 wt-%, based on the total weight of the metal alloy, of Ni, and
(iii) 5 wt-%-15 wt-%, based on the total weight of the metal alloy, of Co, and
(iv) 3.5 wt-%-7 wt-%, based on the total weight of the metal alloy, of Mo.

Therefore, the present invention relates to a powderous catalytic system (IV) which is the powderous catalytic system (I), (I'), (II), (II'), (III) or (III'), wherein the metal alloy carrier is maraging steel.

Another preferred metal alloys are iron/chromium/nickel alloys.

Suitable iron/chromium/nickel alloys comprise
(i) 60 weight-% (wt-%)-80 wt-%, based on the total weight of the metal alloy, of Fe, and
(ii) 1 wt-%-30 wt-%, based on the total weight of the metal alloy, of Cr, and
(iii) 0.5 wt-%-10 wt-%, based on the total weight of the metal alloy, of Ni.

Further suitable iron/chromium/nickel alloys consists of
(i) 60 weight-% (wt-%)-80 wt-%, based on the total weight of the metal alloy, of Fe, and
(ii) 1 wt-%-30 wt-%, based on the total weight of the metal alloy, of Cr, and
(iii) 0.5 wt-%-10 wt-%, based on the total weight of the metal alloy, of Ni.

Therefore, the present invention relates to a powderous catalytic system (V) which is the powderous catalytic system (I), wherein the metal alloy carrier comprises
(i) 60 weight-% (wt-%)-80 wt-%, based on the total weight of the metal alloy, of Fe, and
(ii) 1 wt-%-30 wt-%, based on the total weight of the metal alloy, of Cr, and
(iii) 0.5 wt-%-10 wt-%, based on the total weight of the metal alloy, of Ni.

Therefore, the present invention relates to a powderous catalytic system (V') which is the powderous catalytic system (I), wherein the metal alloy carrier consists of
(i) 60 weight-% (wt-%)-80 wt-%, based on the total weight of the metal alloy, of Fe, and
(ii) 1 wt-%-30 wt-%, based on the total weight of the metal alloy, of Cr, and
(iii) 0.5 wt-%-10 wt-%, based on the total weight of the metal alloy, of Ni.

A suitable and preferred iron/chromium/nickel alloy type is stainless steel.

Three main types of stainless steels are known. These are classified by their crystalline structure: austenitic, ferritic, and martensitic.

The most important type (more than 70% of the stainless steel production volume) is the austenitic steel. Austenitic steels have austenite as their primary phase. These are alloys containing usually between 18 wt-%-20 wt-%, based on the total weight of the alloy, of chromium and 8 wt-%-10 wt-%, based on the total weight of the alloy, of nickel.

Ferritic steels have ferrite as their main phase. These steels contain iron and about 17 wt-%, based on the total weight of the alloy, of chromium.

Martensitic steel has a characteristic orthorhombic martensite microstructure.

Martensitic steels are low carbon steels.

A preferred stainless steel comprises
(i) 60 wt-%-80 wt-%, based on the total weight of the stainless steel carrier, of Fe, and
(ii) 12 wt-%-25 wt-%, based on the total weight of the stainless steel carrier, of Cr, and
(iii) 1 wt-%-8 wt-%, based on the total weight of the stainless steel, of Ni, and
(iv) 1 wt-%-8 wt-%, based on the total weight of the stainless steel carrier, of Cu.

Another preferred stainless steel consists of
(i) 60 wt-%-80 wt-%, based on the total weight of the stainless steel carrier, of Fe, and
(ii) 12 wt-%-25 wt-%, based on the total weight of the stainless steel carrier, of Cr, and
(iii) 1 wt-%-8 wt-%, based on the total weight of the stainless steel, of Ni, and
(iv) 1 wt-%-8 wt-%, based on the total weight of the stainless steel carrier, of Cu.

Therefore, the present invention relates to a powderous catalytic system (VI) which is the powderous catalytic system (I) or (V), wherein the metal alloy carrier is stainless steel comprising
(i) 60 wt-%-80 wt-%, based on the total weight of the stainless steel carrier, of Fe, and
(ii) 12 wt-%-25 wt-%, based on the total weight of the stainless steel carrier, of Cr, and
(iii) 1 wt-%-8 wt-%, based on the total weight of the stainless steel, of Ni, and
(iv) 1 wt-%-8 wt-%, based on the total weight of the stainless steel carrier, of Cu.

Therefore, the present invention relates to a powderous catalytic system (VI') which is the powderous catalytic system (I) or (V), wherein the metal alloy carrier is stainless steel consists of
(i) 60 wt-%-80 wt-%, based on the total weight of the stainless steel carrier, of Fe, and
(ii) 12 wt-%-25 wt-%, based on the total weight of the stainless steel carrier, of Cr, and
(iii) 1 wt-%-8 wt-%, based on the total weight of the stainless steel, of Ni, and (iv) 1 wt-%-8 wt-%, based on the total weight of the stainless steel carrier, of Cu.

Stainless steel is commercially available from many producers and traders. It can be bought i.e. from companies such as Sverdrup Hanssen, Nichelcrom Acciai Inox S.p.A or EOS GmbH.

Suitable products are i.e. EOS StainlessSteel GP1® from EOS GmbH (Germany)

The metal alloys can comprise further metals, such as i.e. Cu, Mn, Si, Ti, Al and/or Nb.

Furthermore the metal alloy can comprise carbon as well.

Therefore, the present invention also relates to a powderous catalytic system (VII), which is the catalytic system (I), (II), (III), (IV), (V) or (VI), wherein the metal alloy comprises at least one further metal chosen from the group consisting of Cu, Mn, Si, Ti, Al and Nb.

Therefore, the present invention also relates to a powderous catalytic system (VIII), which is the catalytic system (I), (II), (III), (IV), (V), (VI) or (VII) wherein the metal alloy comprises carbon.

The metal oxide layer of the embodiment of the present invention (which comprises $CeO_2$), which coats the metal alloy, is non-acidic (preferably basic or amphoteric). Suitable non-acidic metal oxide layers can also comprise at least one further metal oxide wherein the metal is chosen from the group consisting of Zn, Cr, Mn, Mg, Cu and Al.

The metal alloy is preferably coated with a thin layer of metal oxide layer ($CeO_2$) (0.5-3.5 μm thickness) and optionally at least one further metal oxide wherein the metal is chosen from the group consisting of Zn, Cr, Mn, Mg, Cu and Al.

Therefore the present invention also relates to a powderous catalytic system (IX), which is powderous catalytic system (I), (I'), (II), (II'), (III), (III'), (IV), (V), (V'), (VI), (VI'), (VII) or (VIII), wherein the metal alloy is coated with a thin layer of $CeO_2$ and optionally at least one further metal (Cr, Mn, Mg, Cu and/or Al) oxide.

Therefore the present invention also relates to a powderous catalytic system (IX'), which is powderous catalytic system (IX), wherein the layer of metal oxide ($CeO_2$) has a thickness of 0.5-3.5 μm.

The coating of the metal alloy is done by commonly known processes, such as i.e. dip-coating.

Usually the catalytic system (catalyst) of the present invention comprises between 0.1 wt-% and 50 wt-%, based on the total weight of the catalyst, of $CeO_2$, preferably between 0.1 wt-% and 30 wt-%, more preferably between 0.5 wt-% and 5 wt-% and most preferably between 0.5 wt-% and 2 wt-%.

Therefore the present invention also relates to a powderous catalytic system (X), which is powderous catalytic system (I), (I'), (II), (II'), (III), (III'), (IV), (V), (V'), (VI), (VI'), (VII), (VIII), (IX) or (IX'), wherein the catalyst comprises between 0.1 wt-% and 50 wt-%, based on the total weight of the catalytic system, of $CeO_2$ (preferably between 0.1 wt-% and 30 wt-%, more preferably between 0.5 wt-% and 10 wt-% and most preferably between 0.5 wt-% and 2 wt-%).

In a preferred embodiment of the present invention the non-acidic metal oxide layers comprises $CeO_2$ and at least one further metal oxide wherein the metal is chosen from the group consisting of Zn, Cr, Mn, Mg, Cu and Al.

In a more preferred embodiment of the present the non-acidic metal oxide layer comprises $CeO_2$ and $Al_2O_3$.

In an also more preferred embodiment of the present the non-acidic metal oxide layer comprises $CeO_2$ and ZnO.

Therefore the present invention also relates to a powderous catalytic system (XI), which is powderous catalytic system (I), (I'), (II), (II'), (III), (III'), (IV), (V), (V'), (VI), (VI'), (VII), (VIII), (IX), (IX') or (X), wherein the non-acidic metal oxide layer comprises $CeO_2$ and $Al_2O_3$.

Therefore the present invention also relates to a powderous catalytic system (XII), which is powderous catalytic system (I), (I'), (II), (II'), (III), (III'), (IV), (V), (V'), (VI), (VI'), (VII), (VIII), (IX), (IX') or (X), wherein the non-acidic metal oxide layer comprises $CeO_2$ and ZnO.

When a mixture of $CeO_2$ and $Al_2O_3$ is used then it is preferred that the ratio of $CeO_2:Al_2O_3$ is from 2:1 to 1:2 (preferably 1:1).

When a mixture of $CeO_2$ and ZnO is used then it is preferred that the ratio of $CeO_2:ZnO$ is from 2:1 to 1:2 (preferably 1:1).

When using mixture of metal oxides the total content of the metal oxide will not exceed 50 wt-%, based on the total weight of the catalytic system.

Therefore the present invention also relates to a powderous catalytic system (XI'), which is the powderous catalytic system (XI), wherein the ratio of $CeO_2:Al_2O_3$ is from 2:1 to 1:2 (preferably 1:1).

Therefore the present invention also relates to a powderous catalytic system (XI"), which is the powderous catalytic system (XI) or (XI'), wherein the catalyst comprises between 0.1 wt-% and 50 wt-%, based on the total weight of the catalytic system, of metal oxides (preferably between 0.1 wt-% and 30 wt-%, more preferably between 0.5 wt-% and 10 wt-% and most preferably between 0.5 wt-% and 2 wt-%).

Therefore the present invention also relates to a powderous catalytic system (XII'), which is the powderous catalytic system (XII), wherein the ratio of $CeO_2:ZnO$ is from 2:1 to 1:2 (preferably 1:1).

Therefore the present invention also relates to a powderous catalytic system (XII"), which is the powderous catalytic system (XII) or (XII'), wherein the catalyst comprises between 0.1 wt-% and 50 wt-%, based on the total weight of the catalytic system, of metal oxides (preferably between 0.1 wt-% and 30 wt-%, more preferably between 0.5 wt-% and 10 wt-% and most preferably between 0.5 wt-% and 2 wt-%).

The coated metal alloys are then impregnated by Pd-nanoparticles. The nanoparticles are synthesized by commonly known methods, i.e. by using $PdCl_2$ as a precursor, which is then reduced by hydrogen.

It is also possible to use a process, wherein metal alloys are impregnated by the Pd-nanoparticles by a process, which comprises a sonication step. The sonication is the act of applying sound energy to agitate particles in a sample. Ultrasonic frequencies (>20 kHz) are usually used, leading to the process also being known as ultrasonication or ultrasonication.

It is usually applied using an ultrasonic bath or an ultrasonic probe.

Such a process comprises usually (and preferably) the following steps:

(a) preparing an aqueous solution of Pd-salt optionally adding a polyethylene glycol (b) heating the solution of step (a) and subjecting the solution to sonication (c) adding a reducing agent, preferably a solution of formate, to the Pd solution (d) adding the metal oxide powder (e) the suspension which is obtained in step (d) is filtrated and dried In the following the steps of the process wherein a sonication step is involved is discussed in more details below:

Step (a)

The Pd salt is dissolved in water (or aqueous solvent, which means that water is mixed at least one other solvent).

Any commonly known and used Pd-salt can be used. Suitable salts are PdCl$_2$ or Na$_2$PdCl$_4$. It can be one Pd-salt as well as a mixture of two or more Pd-salts.

Furthermore, it is of an advantage to add at least one surfactant to the solution.

Suitable are i.e. polyethylene glycol (PEG), polyvinylpyrrolidones (PVP) or glucosamides.

Step (b)

The solution of step is usually heated up to elevated temperature. Usually not to a higher temperature as the boiling point of the solvent (or solvent mixture used).

Usually it is heated up to a temperature of between 30-80° C.

The sonication is usually carried out at a frequency of 30-50 kHz.

The duration of the sonication step is usually at least 10 minutes, preferred more than 20 (suitable and preferred range is 30-120 minutes). The maximal length of the duration of the sonication step is not critical.

The sonication step can be carried out by using an ultrasonic bath or an immersion probe. Or even a combination of both methods is possible.

Step (c)

To the solution of step (b) a reducing agent is added. Usually it is a sodium formate solution. But also, other formate salts (or mixtures of formate salts) could be used. Optionally (instead of or additionally), it is also possible to add H2-gas, L-ascorbic acid, and/or formic acid.

Step (d)

To the solution of step (c) the metal oxide powder (or a mixture of metal oxide powders) are added. Usually the reaction mixture is stirred.

Step (e)

Finally, the suspension of step (d) is filtered and the obtained doped metal oxide powder is usually washed and dried.

Usually the Pd-nanoparticles, which are on the non-acidic metal oxide layer, have an average particle size of between 0.5 and 20 nm, preferably of between 2 and 15 nm, more preferably of between 5 and 12 nm. (The average particle size can be measured by electron microscopy methods).

Therefore the present invention also relates to a powderous catalytic system (XIII), which is powderous catalytic system (I), (I'), (II), (II'), (III), (III'), (IV), (V), (V'), (VI), (VI'), (VII), (VIII), (IX), (IX'), (X), (XI), (XI'), (XI"), (XII), (XII') or (XII"), wherein the Pd-nanoparticles have an average particle size of between 0.5 and 20 nm (preferably of between 2 and 15 nm, more preferably of between 5 and 12 nm).

The catalyst according to present invention comprises between 0.001 wt-% and 5 wt-%, based on the total weight of the catalyst, of the Pd-nanoparticles, preferably between 0.01 wt-% and 2 wt-% more preferably between 0.05 wt-% and 1 wt-%.

Therefore the present invention also relates to a powderous catalytic system (XIV), which is the powderous catalytic system (I), (I'), (II), (II'), (III), (III'), (IV), (V), (V'), (VI), (VI'), (VII), (VIII), (IX), (IX'), (X), (XI), (XI'), (XII), (XII') or (XIII), wherein the catalyst comprises between 0.001 wt-% and 5 wt-%, based on the total weight of the catalyst, of the Pd-nanoparticles (preferably between 0.01 wt-% and 2 wt-% more preferably between 0.05 wt-% and 1 wt-%).

The catalyst is usually activated before the use. The activation is done by using well known processes, such as thermal activation under H$_2$.

The catalyst of the present invention is used in selective catalytic hydrogenation of organic starting material, especially of organic starting material comprising a carbon-carbon triple bond, more especially of alkynol compounds.

Therefore the present invention also relates to the use of a powderous catalytic system (catalyst) (I), (I'), (II), (II'), (III), (III'), (IV), (V), (V'), (VI), (VI'), (VII), (VIII), (IX), (IX'), (X), (XI), (XI'), (XI"), (XII), (XII'), (XII"), (XIII) or (XIV), in selective catalytic hydrogenation of organic starting material, especially of organic starting material comprising a carbon-carbon triple bond, more especially of alkynol compounds.

Preferably the present invention relates to a process of reacting a compound of formula (I)

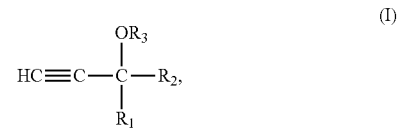

(I)

wherein

R$_1$ is linear or branched C$_1$-C$_{35}$ alkyl or linear or branched C$_5$-C$_{35}$ alkenyl moiety, wherein the C chain can be substituted, and R$_2$ is linear or branched C$_1$-C$_4$ alkyl, wherein the C chain can be substituted, R$_3$ is H or —C(CO)C$_1$-C$_4$alkyl, with hydrogen in the presence of a catalyst ((I), (II), (III), (IV), (V), (VI), (VIII), (IX), (X), (XI), (XI'), (XI"), (XII), (XII'), (XII"), (XIII) or (XIV).

Therefore the present invention relates to a process (P) of reacting a compound of formula (I)

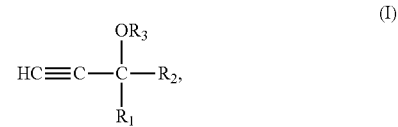

(I)

wherein

R$_1$ is linear or branched C$_1$-C$_{35}$ alkyl or linear or branched C$_5$-C$_{35}$ alkenyl moiety, wherein the C chain can be substituted, and R$_2$ is linear or branched C$_1$-C$_4$ alkyl, wherein the C chain can be substituted, R$_3$ is H or —C(CO)C$_1$-C$_4$alkyl, with hydrogen in the presence of a catalyst (I), (II), (III), (IV), (V), (VI), (VIII), (IX), (X), (XI), (XI'), (XI"), (XII), (XII'), (XII"), (XIII) or (XIV).

Hydrogen is usually used in the form of H$_2$ gas.

Therefore the present invention relates to a process (P1), which process (P), wherein hydrogen is usually used in the form of H$_2$ gas.

Preferred compounds of formula (I) are the following:

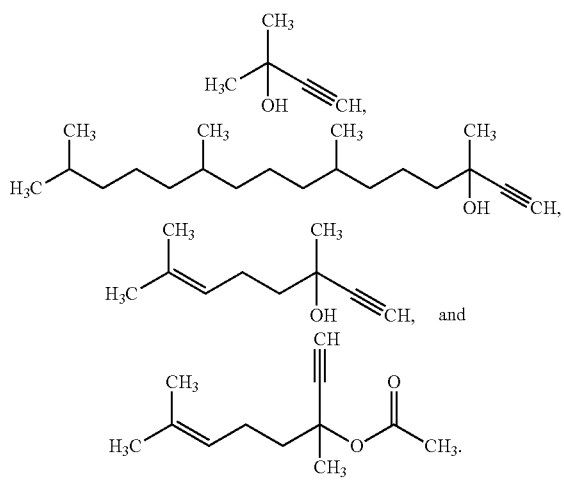

Therefore the present invention relates to a process (P2), which process (P) or (P1), wherein, the following compounds

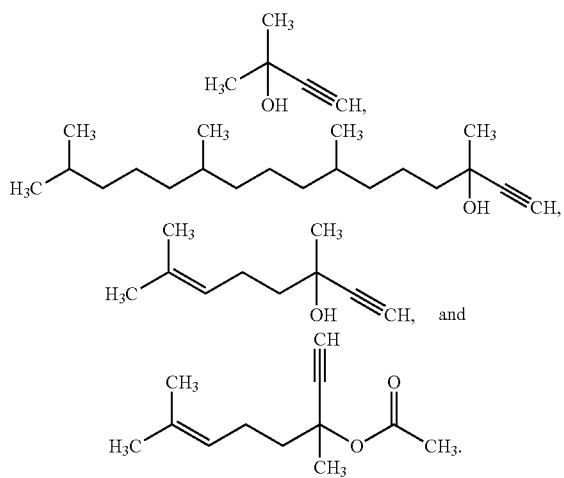

are hydrogenated selectively.

The following examples serve to illustrate the invention. All percentages are related to weight and the temperatures are given in degree Celsius, if not otherwise stated.

EXAMPLES

Example 1

Preparation of Metal Powder Catalyst

The EOS MaragingSteel MS1 was heated at 450° C. for 3 h in air. For preparation of the primer solution, Ce(NO$_3$)$_3$.6H$_2$O (508 mmol) and 700 mL water were added to a beaker. The mixture was stirred until the salt was completely dissolved. The solution was heated to 90° C. and ZnO (508 mmol) was slowly added to the solution. The stirring was maintained at 90° C. and 65% nitric acid was added dropwise until all ZnO was completely dissolved (final $c_{HNO3}$=1 M). Afterwards the solution was cooled to room temperature and filtrated through a 0.45 μm membrane filter. The deposition of ZnO/CeO$_2$ was performed by adding thermally treated MS1 powder (10.0 g) to 25 mL of the precursor solution. This mixture was stirred at room temperature for 15 min. Afterwards the suspension was filtered via a 0.45 μm membrane filter and dried under vacuum at 40° C. for 2 h followed by calcination at 450° C. for 1 h. This process was repeated until the desired number of primer layers had been deposited.

Sodium tetrachloropalladate(II) (0.48 mmol) was dissolved in 133 mL of Millipore water and PEG-MS40 (3.2 mmol) was added. The solution was heated to 60° C. and sonication was started at this temperature. A fresh prepared solution of sodium formate (16 mM, 67 mL) were added. The solution was sonicated for further 60 minutes at this temperature and then cooled to room temperature followed by addition of the coated MS1 (10.0 g). The suspension was stirred at room temperature for 60 minutes followed by filtration via a 0.45 μm membrane filter. The residue was washed with water and dried under vacuum at 40° C. for 2 h. The catalyst was subjected to a temperature treatment between 150° C.-350° C. for 4 h (temperature ramp—10°/min) under H$_2$—Ar flow (1:9; total flow rate—450 ml/min).

Hydrogenation Examples

Selective Semi-Hydrogenation of an Alkyne to an Alkene 40.0 g of 2-methyl-3-butyne-2-ol (MBY) and the desired amount of metal powder catalyst were added to a 125 mL autoclave reactor. Isothermal conditions during the hydrogenation reaction (338 K) were maintained by a heating/cooling jacket. The reactor was equipped with a gas-entrainment stirrer. After purging with nitrogen, the reactor was purged with hydrogen and heated to the desired temperature. The pressure in the reactor (3.0 bar) was maintained during the experiments by supplying hydrogen from external reservoir. The reaction mixture was stirred at 1000 rpm. Liquid samples (200 μL) were periodically withdrawn from the reactor starting at a minimum conversion of 95% of MBY and analysed by gas-chromatography (HP 6890 series, GC-system). Selectivity is reported as amount of the desired semi-hydrogenation product (2-methyl-3-butene-2-ol (MBE)) compared to all reaction products.

Tables 1a and 1b: Test Results of Different Oxide Layers, Pd-Source, Pd-Amount and Pd-Reduction The catalysts prepared according to the process described in the example above and they were thermal activated as mentioned in the preparation procedure Reaction conditions: 500 mg catalyst, 40.0 MBY, 1000 rpm, 3.0 bar H$_2$, 65° C. Exp. 1 is a comparison example using a oxide layer known from the prior art.

TABLE 1a

| Exp | Oxide Layer & Layer # | Pd-source (loading wt %) | Pd-reduction procedure |
|---|---|---|---|
| 1 | Al$_2$O$_3$/ZnO (3) | PdCl$_2$ (0.50) | H$_2$ bubbling (25° C.) |
| 2 | CeO$_2$/ZnO (3) | Na$_2$PdCl$_4$ (0.50) | H$_2$ bubbling (25° C.) |
| 3 | CeO$_2$/ZnO (5) | Na$_2$PdCl$_4$ (0.35) | HCOONa, PEG, sonication (60° C.) |

TABLE 1b

| Exp | Conv. (%) | Time (min) | Select. (%) | Activity (mmol/sg$_{Pd}$) |
|---|---|---|---|---|
| 1 | 99.9 | 195 | 95.1 | 247.1 |
| 2 | 99.7 | 125 | 96.0 | 315.8 |
| 3 | 99.7 | 107 | 97.0 | 535.5 |

It can be seen that the new metal oxide powders show an improved selectivity and an improved activity.

TABLE 2

Test results at varying metal oxide layer thickness of CeO$_2$/ZnO and Pd-amount (Na$_2$PdCl$_4$ reduced with HCOONa/sonication/PEG at 60° C.),

| Exp | Metal oxide layers # | Pd-loading (wt %) | Conv (%) | Time (min) | Select. (%) | Activity (mmol/sg$_{Pd}$) |
|---|---|---|---|---|---|---|
| 4 | 3 | 0.20 | 99.7 | 119 | 96.64 | 733.6 |
| 5 | 3 | 0.35 | 99.6 | 92 | 96.66 | 582.5 |
| 6 | 3 | 0.50 | 99.7 | 134 | 96.33 | 353.0 |
| 7 | 5 | 0.20 | 99.6 | 120 | 96.70 | 630.6 |
| 8 | 5 | 0.35 | 99.7 | 112 | 96.84 | 508.8 |
| 9 | 5 | 0.50 | 99.6 | 105 | 96.28 | 366.4 |
| 10 | 8 | 0.20 | 99.7 | 151 | 96.73 | 553.1 |
| 11 | 8 | 0.35 | 99.7 | 171 | 96.44 | 474.1 |
| 12 | 8 | 0.50 | 99.7 | 157 | 96.22 | 355.8 |

The catalysts prepared according to the process described in the example above and they were thermal activated as mentioned in the preparation procedure
Reaction conditions: 500 mg catalyst, 40.0 MBY, 1000 rpm, 3.0 bar H$_2$, 65° C.

TABLE 3

Test results at varying thermal activation temperatures; 5 layersCeO$_2$/ZnO and 0.35 wt % Pd (Na$_2$PdCl$_4$ reduced with HCOONa/sonication/PEG at 60° C.

| Exp. | Activation temp (° C.) | Conv. (%) | Time (min) | Select. (%) | Activity (mmol/sg$_{Pd}$) |
|---|---|---|---|---|---|
| 13 | 200 | 99.7 | 103 | 96.9 | 538.1 |
| 14 | 250 | 99.7 | 107 | 97.0 | 535.5 |
| 15 | 300 | 99.9 | 112 | 96.6 | 508.8 |
| 16 | 350 | 99.8 | 127 | 96.2 | 464.0 |

The catalysts prepared according to the process described in the example above.
Reaction Conditions: 500 mg catalyst, 40.0 MBY, 1000 rpm, 3.0 bar H$_2$, 65° C.

The invention claimed is:

1. A method for selective hydrogenation of an organic starting material comprised of a compound of formula (I):

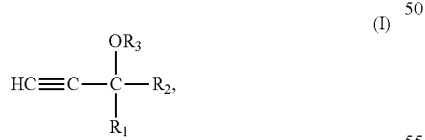

(I)

wherein,
R$_1$ is linear or branched C$_1$-C$_{35}$ alkyl or linear or branched C$_5$-C$_{35}$ alkenyl moiety, wherein the C chain can be substituted,
R$_2$ is linear or branched C$_1$-C$_4$ alkyl, wherein the C chain can be substituted, and
R$_3$ is H or —C(CO)C$_1$-C$_4$alkyl, wherein
the method comprises subjecting the organic starting material comprised of the compound of formula (I) to selective hydrogenation conditions in the presence of hydrogen and a powderous catalytic system comprising a metal alloy carrier which is impregnated with Pd and coated by a metal oxide layer comprised of CeO$_2$, wherein the metal alloy carrier comprises, based on the total weight of the metal alloy:
(i) 45 wt. % to 80 wt-% of Fe,
(ii) 0.5 wt. % to 30 wt. % of Ni,
(iii) 0 wt. % to 20 wt. % of Co,
(iv) 0 wt. % to 8 wt. % of Mo, and
(v) 0 wt. % to 30 wt-% of Cr.

2. The method according to claim 1, wherein the organic starting material comprises at least one compound selected from the group consisting of:

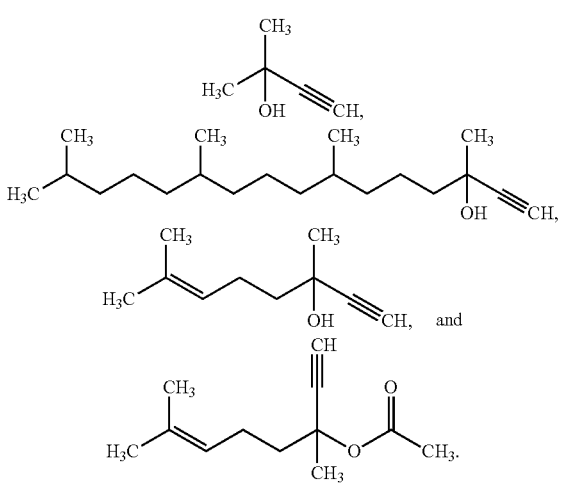

3. The method according to claim 1, wherein the hydrogen of the hydrogenation step is H$_2$ gas.

4. The method according to claim 1, wherein the metal alloy carrier comprises, based on the total weight of the metal alloy:
(i) 45 wt. % to 75 wt. % of the Fe,
(ii) 15 wt. % to 30 wt. % of the Ni,
(iii) 5 wt. % to 20 wt. % of the Co, and
(iv) 3 wt. % to 8 wt. % of the Mo.

5. The method according to claim 1, wherein the metal alloy carrier comprises, based on the total weight of the metal alloy:
(i) 60 wt. % to 70 wt. % of the Fe,
(ii) 15 wt. % to 25 wt. % of the Ni,
(iii) 5 wt. % to 15 wt. % of the Co, and
(iv) 3.5 wt. % to 7 wt. % of the Mo.

6. The method according to claim 1, wherein the metal alloy carrier comprises, based on the total weight of the metal alloy:
(i) 60 wt. % to 80 wt. % of the Fe,
(ii) 1 wt. % to 30 wt. % of the Cr, and
(iii) 0.5 wt. % to 10 wt. % of the Ni.

7. The method according to claim 1, wherein the metal alloy carrier comprises at least one further metal selected from the group consisting of Cu, Mn, Si, Ti, Al and Nb.

8. The method according to claim 1, wherein metal alloy carrier comprises carbon.

9. The method according to claim 1, wherein the metal alloy carrier is coated with at least one further metal oxide comprising an oxide of a metal selected from the group consisting of Cr, Mn, Zn, Cu and Al.

10. A selective hydrogenation reaction system comprising:

(a) an organic reactant comprised of a compound of formula (I):

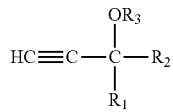

wherein,
R$_1$ is linear or branched C$_1$-C$_{35}$ alkyl or linear or branched C$_5$-C$_{35}$ alkenyl moiety, wherein the C chain can be substituted,
R$_2$ is linear or branched C$_1$-C$_4$ alkyl, wherein the C chain can be substituted, and R$_3$ is H or —C(CO) C$_1$-C$_4$alkyl, and
(b) a metal alloy carrier which is impregnated with Pd and coated by a metal oxide layer comprised of CeO$_2$, wherein the metal alloy carrier comprises, based on the total weight of the metal alloy:
(i) 45 wt. % to 80 wt-% of Fe,
(ii) 0.5 wt. % to 30 wt. % of Ni,
(iii) 0 wt. % to 20 wt. % of Co,
(iv) 0 wt. % to 8 wt. % of Mo, and
(v) 0 wt. % to 30 wt-% of Cr.

11. The selective hydrogenation reaction system according to claim 10, wherein the metal alloy carrier comprises, based on total weight of the metal alloy:
(i) 45 wt. % to 75 wt. % of the Fe,
(ii) 15 wt. % to 30 wt. % of the Ni,
(iii) 5 wt. % to 20 wt. % of the Co, and
(iv) 3 wt. % to 8 wt. % of the Mo.

12. The selective hydrogenation reaction system according to claim 10, wherein the metal alloy carrier comprises, based on total weight of the metal alloy:
(i) 60 wt. % to 70 wt. % of the Fe
(ii) 15 wt. % to 25 wt. % of the Ni,
(iii) 5 wt. % to 15 wt. % of the Co, and
(iv) 3.5 wt. % to 7 wt. % of the Mo.

13. The selective hydrogenation system according to claim 10, wherein the metal alloy carrier comprises, based on total weight of the metal alloy:
(i) 60 wt. % to 80 wt. % of the Fe,
(ii) 1 wt. % to 30 wt. % of the Cr, and
(iii) 0.5 wt. % to 10 wt. % of the Ni.

14. The selective hydrogenation system according to claim 10, wherein the metal alloy carrier comprises at least one further metal selected from the group consisting of Cu, Mn, Si, Ti, Al and Nb.

15. The selective hydrogenation system according to claim 10, wherein metal alloy carrier comprises carbon.

16. The selective hydrogenation reaction system according to claim 10, wherein the metal alloy carrier is coated with at least one further metal oxide comprising an oxide of a metal selected from the group consisting of Cr, Mn, Zn, Cu and Al.

* * * * *